United States Patent
Voegele et al.

(10) Patent No.: US 8,792,966 B2
(45) Date of Patent: Jul. 29, 2014

(54) TRANSLUMINAL TISSUE MARKERS

(75) Inventors: James W. Voegele, Cincinnati, OH (US);
William B. Weisenburgh, II,
Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1516 days.

(21) Appl. No.: 12/041,390

(22) Filed: Mar. 3, 2008

(65) Prior Publication Data
US 2009/0221915 A1   Sep. 3, 2009

(51) Int. Cl.
*A61B 6/00* (2006.01)
*A61B 19/00* (2006.01)

(52) U.S. Cl.
CPC ............................. *A61B 19/54* (2013.01)
USPC ..................... 600/431; 128/899; 606/151

(58) Field of Classification Search
CPC .... A61B 19/54; A61B 17/11; A61B 17/0057; A61B 2017/00606
USPC ................... 600/431–435; 128/897–898, 899; 606/116, 151, 153, 155, 157, 231, 215
See application file for complete search history.

(56) References Cited

U.S. PATENT DOCUMENTS

| | | | | |
|---|---|---|---|---|
| 5,853,422 A * | 12/1998 | Huebsch et al. | ............... | 606/213 |
| 6,766,186 B1 * | 7/2004 | Hoyns et al. | ................... | 600/431 |
| 2003/0149463 A1 | 8/2003 | Solymar et al. | | |
| 2003/0225420 A1 * | 12/2003 | Wardle | .......................... | 606/151 |
| 2004/0254594 A1 | 12/2004 | Alfaro | | |
| 2005/0049633 A1 | 3/2005 | Watanabe | | |
| 2005/0049634 A1 | 3/2005 | Chopra | | |
| 2005/0070935 A1 * | 3/2005 | Ortiz | .............................. | 606/153 |
| 2006/0224183 A1 | 10/2006 | Freudenthal | | |
| 2008/0039676 A1 * | 2/2008 | Fischell et al. | .................. | 600/12 |

FOREIGN PATENT DOCUMENTS

FR          2714284 A1     6/1995

OTHER PUBLICATIONS

European Search Report, Application No. 09250584.1, Mailed Jun. 17, 2009, 9 pages.
Chinese Office Action, Application No. 20090126423.7 mailed Jan. 31, 2012.

* cited by examiner

*Primary Examiner* — Charles A Marmor, II
*Assistant Examiner* — Carrie R Dorna
(74) *Attorney, Agent, or Firm* — Mintz Levin Cohn Ferris Glovsky and Popeo, P.C.

(57) ABSTRACT

Methods and devices are provided for marking tissue to be subsequently located for removal from a body or for other examination. In general, a marker is provided that can be delivered through a tissue wall proximate to tissue desirable for marking. The marker can be movable between a non-deployed or unexpanded position, in which the marker is configured to be delivered through a relatively small diameter passageway, to an expanded, balloon-like position in which the marker is configured to engage opposed sides of a tissue wall proximate to the desired tissue. The marker can remain disposed in the body in its expanded position and be subsequently palpably identified and/or visually identified to locate the desired tissue.

6 Claims, 7 Drawing Sheets

TRANSLUMINAL TISSUE MARKERS

FIELD OF THE INVENTION

The present invention relates to transluminal tissue markers and methods for marking tissue transluminally.

BACKGROUND OF THE INVENTION

Colonoscopy is an outpatient procedure in which the rectum and the inside of the lower large intestine (colon) are examined. Colonoscopies are commonly used to evaluate bowel disorders, rectal bleeding or polyps (usually benign growths) found on contrast x-rays. Colonoscopies are also performed to screen people over age 50 for colon and rectal cancer. During a colonoscopy, a physician uses a colonoscope (a long, flexible instrument about ½ inch in diameter) to view the lining of the colon. The colonoscope is inserted through the rectum and advanced to the large intestine.

If necessary during a colonoscopy, small amounts of tissue can be removed for analysis (called a biopsy) and polyps can be identified and removed. In many cases, colonoscopy allows accurate diagnosis and treatment without the need for a major operation. However, in some cases the tissue cannot be removed during the colonoscopy, and thus must be removed in a subsequent surgical procedure. In these situations, india ink or blue dye is topically injected during the preoperative colonoscopy to mark the tumor site. However, such a procedure includes the intrinsic danger of possibly injecting dye into the peritoneal cavity. In addition, the injected marker may also spread so widely that the intended site may become obscured.

Accordingly, there remains a need for improved methods and devices for marking tissue, such as the bowel wall.

SUMMARY OF THE INVENTION

The present invention generally provides methods and devices for marking tissue to be subsequently located for removal from a body or for other examination. In one aspect, a method for marking tissue is provided that includes identifying tissue to be removed, positioning a marker through a tissue wall e.g., a bowel wall) proximate to the tissue to be removed, and expanding proximal and distal portions of the marker on opposing sides of the tissue wall such that the proximal and distal portions engage tissue therebetween and the marker identifies the tissue to be removed. The marker can be positioned through the tissue wall in a variety of ways. For example, positioning the marker can include advancing a delivery device with the marker disposed therearound through the tissue wall to position the proximal and distal portions of the marker on opposing sides of the tissue wall. The proximal and distal portions of the marker can be expanded in a variety of ways, such as by inflating or by permanently deforming the proximal and distal portions. After the proximal and distal portions have been expanded, the marker can be palpably and/or visually identified to locate the tissue to be removed.

In another aspect, a method for marking tissue can include identifying a portion of tissue to be removed, advancing an elongate tubular body in an unexpanded position through a tissue wall proximate to the portion of tissue to be removed, and expanding proximal and distal portions of the tubular body from the unexpanded position to an expanded position to engage a portion of the tissue wall therebetween and to mark a location proximate to the portion of tissue to be removed. The method can also include locating the tubular body to locate the portion of tissue to be removed. The method can further include, after expanding the proximal and distal portions of the tubular body, locking the proximal and distal portions in expanded positions with at least one self-sealing valve.

The tubular body can be advanced in an unexpanded position through a tissue wall in a variety of ways. For example, a delivery device can be advanced through the tissue wall with the tubular body removably coupled thereto and the proximal and distal portions of the tubular body unexpanded. In some embodiments, the delivery device can be removed from the tubular body after the proximal and distal portions have been expanded. The method can also include puncturing the tissue wall using the delivery device prior to advancing the tubular body through the tissue wall.

The proximal and distal portions of the marker can be expanded in a variety of ways, such as by inflating the proximal and distal portions. As another example, the proximal and distal portions can be formed from a shape memory material, and expanding proximal and distal portions of the tubular body can include permanently deforming the proximal and distal portions.

In another aspect, a tissue marking system is provided. The system includes a pliable marker that can be disposable in an unexpanded position through a tissue wall proximate to tissue to be removed. The marker can include proximal and distal portions that can each expand into an expanded position on opposing sides of the tissue wall to engage tissue therebetween and to mark a location proximate to the tissue to be removed.

The marker can be made from any number and any combination of materials, such as the proximal and distal portions each being formed from a shape memory material. The marker can also have any size, shape, and configuration. In some embodiments, the marker is in the form of an elongate tubular body. The marker can also have a nonexpandable middle portion between the proximal and distal portions. In another embodiment, the marker's proximal and distal portions can each include at least one self sealing valve that can secure the proximal and distal portion in the expanded position. The marker can include other features, such as at least one shoulder that can engage the tissue wall to position the proximal and distal portions on opposing sides of a tissue wall having the marker disposed therearound and prevent the marker from passing through the tissue wall.

The system can also include a delivery device that can introduce the marker through the tissue wall and expand each of the proximal and distal portions of the marker into the expanded positions. The delivery device can inflate the marker's proximal and distal portions by, for example, including an inflation port that can receive an inflation fluid to inflate the proximal and distal portions.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
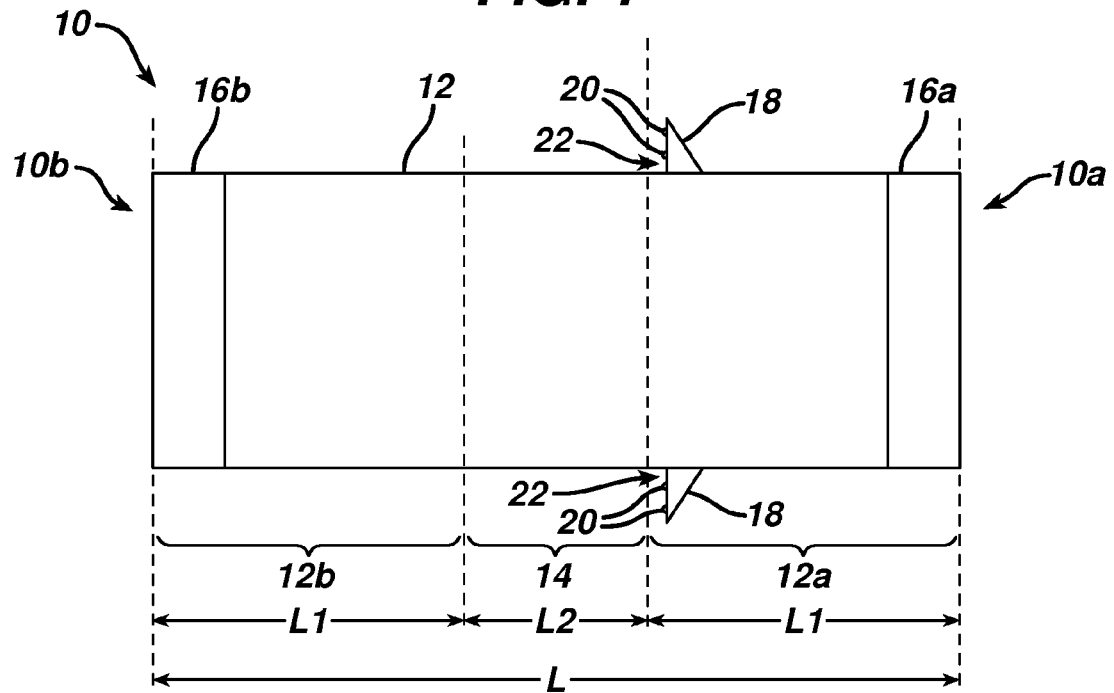
FIG. 1 is a side view of one exemplary embodiment of a marking device in a non-deployed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for marking tissue to be subsequently located for removal from a body or for other examination. While the methods and devices disclosed herein can be used in conventional, open surgical procedures, they are particularly useful in minimally invasive surgical procedures, particularly hand assisted laparoscopic surgery (HALS) and endoscopic procedures. The principles described herein can be applicable to the particular types of tools described herein and to a variety of other surgical tools having similar functions. In addition, the tools can be used alone in a surgical procedure, or they can be used in conjunction with other devices that facilitate minimally invasive surgical procedures. A person skilled in the art will appreciate that the present invention has application in conventional endoscopic and open surgical instrumentation as well application in robotic-assisted surgery.

In general, a marker is provided that can be delivered through a tissue wall proximate to tissue desirable for marking. In an exemplary embodiment, the marker is movable between a non-deployed or unexpanded position, in which the marker is configured to be delivered through a relatively small diameter passageway, to an expanded, balloon-like position in which the marker is configured to engage opposed sides of a tissue wall proximate to the desired tissue. The term "proximate" as used herein is intended to encompass placement on and/or placement near a desired tissue. The marker can remain disposed in the body in its expanded position and be subsequently palpably identified and/or visually identified to locate the desired tissue. While the marker can be used to mark any tissue for any purpose, in an exemplary embodiment the marker is configured for delivery through the working channel of a delivery device and for use in marking tissue for removal from the body, e.g., a polyp or other tissue growth identified during a colonoscopy and intended to be removed from the bowel wall during a subsequent surgical procedure.

The marker can have a variety of configurations. In one exemplary embodiment, shown in FIG. 1, a marker 10 is in the form of a generally elongate tubular body 12 in an initial, unexpanded configuration with a proximal end 10a and a distal end 10b. The marker 10 can include one or more portions that expand to engage tissue therebetween and thereby mark a location of tissue to be removed from the body or to be otherwise examined. In the embodiment shown in FIG. 1, the marker 10 includes proximal and distal portions 12a, 12b configured to expand to engage tissue therebetween. While various techniques can be used to expand the proximal and distal portions 12a, 12b, in an exemplary embodiment, the proximal and distal portions 12a, 12b are each formed from a pliable material that allows the proximal and distal portions 12a, 12b to each move from an unexpanded position into an expanded position where the proximal and distal portions 12a, 12b are each inflated or deformed, as discussed further below. A mid-portion 14 of the tubular body 12, located between the proximal and distal portions 12a, 12b, can be positioned to engage a tissue wall when the marker 10 is advanced through the tissue wall in its unexpanded position. The mid-portion 14 can be formed of a non-pliable material such that when the proximal and/or distal portions 12a, 12b move to expanded positions on opposing sides of the tissue wall, the mid-portion 14 remains in an unexpanded position. The length L2 of the mid-portion 14 is preferably less than the length L1 of the proximal and distal portions 12a, 12b. The proximal and distal portions 12a, 12b can each have any length L1 in the unexpanded position (where L1 can be the same or different for each of the proximal and distal portions 12a, 12b), and the mid-portion 14 can have any length L2. The proximal and distal portions 12a, 12b and the mid-portion 14 can each also have any diameter that is the same or different along their respective lengths and that is the same or different from the diameters of the other portions 12a, 12b, 14. However, the proximal and distal portions 12a, 12b preferably have the same length L1 and the same diameter to help provide for balanced expansion against opposing sides of a tissue wall when the proximal and distal portions 12a, 12b are expanded.

As further shown in FIG. 1, the marker 10 can include proximal and distal self-sealing ends 16a, 16b to aid in the expansion of the proximal and distal portions 12a, 12b, as discussed further below. The self-sealing ends 16a, 16b can be formed from self-sealing valves (e.g., duck bill valves), but the self-sealing ends 16a, 16b can have any configuration and can be composed of any material, preferably a self-sealing elastomer such as silicone. In a preferred embodiment, the self-sealing ends 16a, 16b extend circumferentially around the proximal and distal ends 10a, 10b of the tubular body 12. Such a configuration allows the self-sealing ends 16a, 16b to provide a fluid-tight seal around the circumference of the proximal and distal ends 10a, 10b when the proximal and distal portions 12a, 12b are expanded so as to help fix the proximal and distal portions 12a, 12b in their expanded positions. In some embodiments, the ends 16a, 16b may not be self-sealing but instead can be manually sealable, such as by sutures, adhesive or other bonding material, or other appropriate sealing mechanism. Furthermore, one of the proximal and distal ends 10a, 10b, preferably the distal end 10b, can be permanently closed, and the other end, preferably the proximal end 10a, can be open such that the marker 10 resembles a balloon with one open end to help ease introduction of the marker 10 into the body and to help prevent leakage of any fluid contained within the marker's inner pathway 24. Alternatively, both the proximal and distal ends 10a, 10b could be permanently closed.

The marker 10 can also optionally include one or more shoulders 18 extending substantially perpendicularly from the tubular body's outside surface. The shoulders 18 can extend around any portion of the tubular body's circumference but are preferably located on the mid-portion 14 and/or the proximal portion 12a as a continuous circumferential shoulder 18 or as one or more discrete shoulders 18. The shoulders 18 can help prevent the marker 10 from passing through a tissue wall when the marker 10 is advanced distally through the tissue wall, as discussed further below. The shoulders 18 can be rigid or flexible. The shoulders 18 can also be biased to a substantially perpendicular extended position such that the shoulder 18 can collapse when the marker 10 is disposed within a delivery device for introduction into a body (discussed further below) and "spring" to the extended position when the shoulders 18 are advanced out of the delivery device.

The shoulders 18 can also optionally include one or more tissue engaging mechanisms 20 formed on or attached to a distal, tissue-engaging portion 22 thereof which can be configured to grasp (e.g., grip, hold, penetrate, and/or puncture) tissue engaged by the marker 10. The shoulders 18 can include any number of tissue engaging mechanisms 20, and the tissue engaging mechanisms 20 can have any configuration on the shoulders 18. For example, as shown in FIG. 1, the tissue engaging mechanisms 20 can be in the form of protrusions, e.g., raised bumps and/or a textured surface, located on some or all of an exterior surface of the tissue-engaging portion 22 of the shoulders 18 that can grip tissue. In another example, the tissue engaging mechanisms 20 can be in the form of gripping hooks attached to the tubular body 12 that can penetrate and/or puncture tissue. The tissue engaging mechanisms 20 can facilitate anchoring of the marker 10 proximate to tissue desired for marking. One or more sutures (e.g., purse string sutures) can help secure the elongate tubular body 12 to tissue such that when a suture is pulled tight around the tissue, tissue can be compressed into a tissue engaging mechanism 20 (e.g., a slot) or be prevented from moving by a tissue engaging mechanism 20 (e.g., a dimple). Even in the absence of the shoulders 18 and/or the tissue engaging mechanisms 20, one or more sutures can be similarly used to help secure tissue to the tubular body 12.

Figure 2:
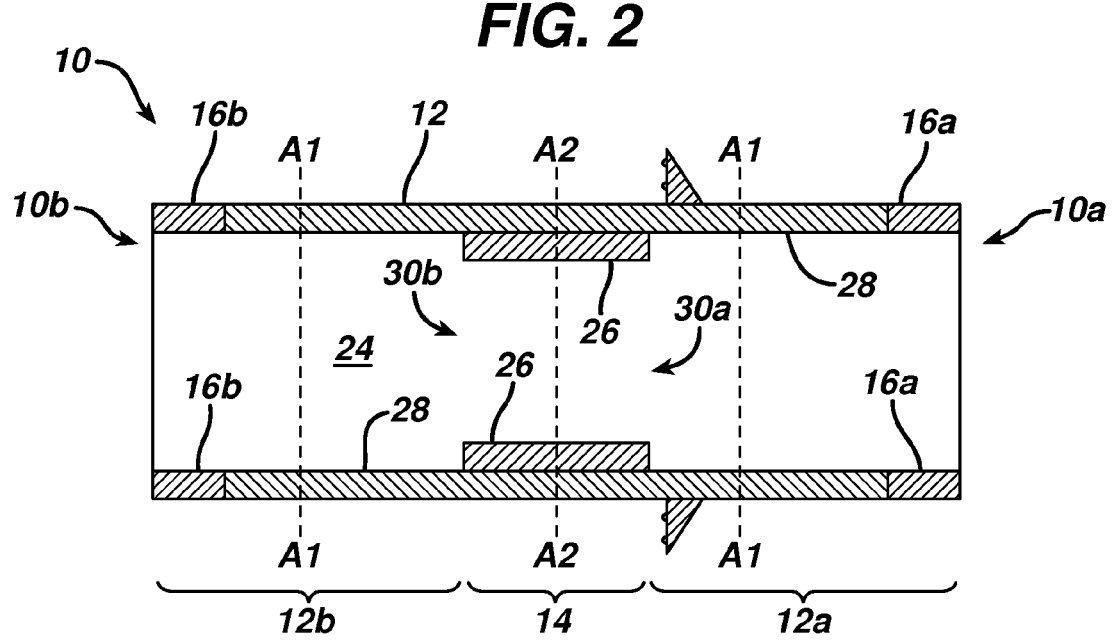
FIG. 2 is a cross-sectional view of a middle portion of the marking device of FIG. 1 showing a bushing.

The marker 10 is shown in an unexpanded position in a cross-sectional configuration in FIG. 2. The tubular body 12 includes the inner pathway 24 extending longitudinally therethrough, through which an introducer device or any other tool can be disposed to introduce the marker 10 into a body, as discussed further below. The inner pathway 24 in the proximal and distal portions 12a, 12b can inflate (e.g., increase in volume) when the marker 10 moves from the non-deployed, unexpanded position to the expanded position. Conversely, the inner pathway 24 in the mid-portion 14 can remain substantially the same (e.g., maintain its volume) when the marker 10 moves from the unexpanded position to the expanded position. The tubular body's mid-portion 14 can optionally include a non-pliable bushing 26 disposed therein that can help prevent the mid-portion 14 from expanding when the marker 10 is inflated or deformed in the proximal and distal portions 12a, 12b. The bushing 26 can also help allow tools and/or fluid to pass through the inner pathway 24 in the mid-portion 14.

The bushing 26 disposed in the mid-portion 14 of the tubular body 12 can optionally be attached to or integrated at least partially into an inner surface 28 of the tubular body 12, e.g., using a temporary or permanent bonding material such as a biocompatible adhesive. Similar to the tubular body 12, the bushing can be in the form of a generally elongate tubular body that extends circumferentially along the tubular body's inner surface 28 with an open distal end 30a and an open proximal end 30b. Although, in some embodiments, the bushing 26 can include one or more discrete bushings having any spacing along and configuration on the tubular body 12. Furthermore, rather than being disposed within the tubular body 12, the bushing 26 can be part of the tubular body 12 such that the tubular body 12 includes at least three discrete portions, namely proximal and distal portions 12a, 12b formed from a pliable material that is attached on opposite sides to non-pliable material in the mid-portion 14.

Figure 3:
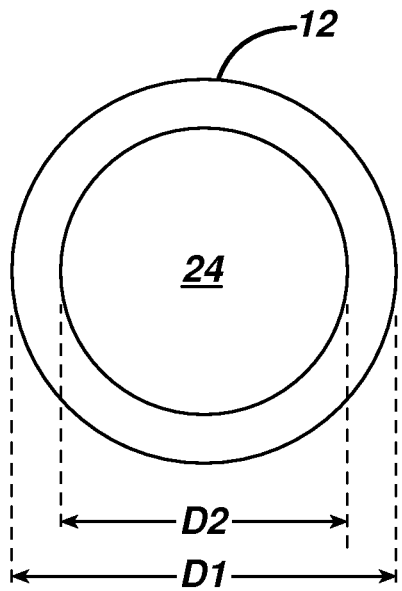
FIG. 3 is a cross-sectional view of the marking device of FIG. 1 taken across line A1-A1.
Figure 4:
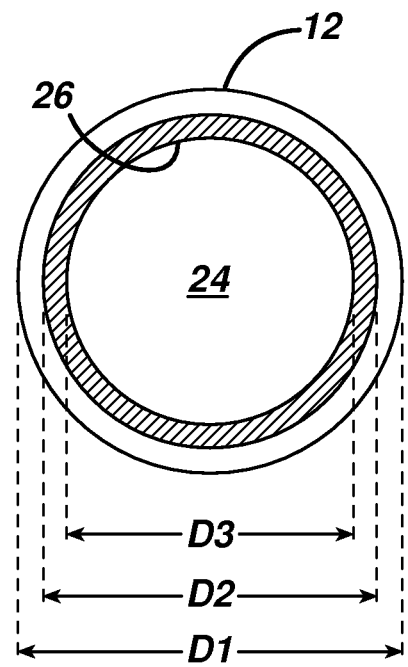
FIG. 4 is a cross-sectional view of a middle portion of the marking device of FIG. 1 taken across line A2-A2.

FIGS. 3 and 4 show cross-sectional views of the marker 10 in its unexpanded position for the proximal and distal portions 12a, 12b (FIG. 3) and for the mid-portion 14 (FIG. 4). The marker 10 has a substantially circular cross-sectional shape along its length L in the unexpanded position, as shown in FIGS. 3 and 4, but the marker 10 can have any cross-sectional shape (e.g., elliptical, rectangular, square, etc.). Furthermore, the marker's cross-sectional shape can vary along the length L of the tubular body 12. The proximal and distal portions 12a, 12b can have the same or different cross-sectional shapes as each other and as the mid-portion 14, although the proximal and distal portions 12a, 12b preferably have the same cross-sectional shape to help provide stability to the marker 10 when the marker 10 is in the expanded position.

In the cross-section shown in FIG. 3, the tubular body 12 in the unexpanded position has an outer diameter D1 and an inner diameter D2. The outer diameter D1 can be configured to allow the tubular body 12 to fit within a body lumen and/or to fit within an introducer for guiding the marker 10 to a desired tissue site, as will be discussed in more detail below. The inner diameter D2 defines the inner pathway 24 of the marker 10 in the unexpanded position and can be configured so that the tubular body 12 can be disposed around a delivery device for delivering the marker 10 into the body, also discussed further below. In the cross-section shown in FIG. 4, the mid-portion 14 includes an inner diameter D3 that remains substantially constant in the marker's unexpanded and expanded positions. The tubular body's inner and outer diameters D2, D1 are the same in both FIGS. 3 and 4 (e.g., when the marker 10 is in the unexpanded position), but as mentioned above, the inner and outer diameters D2, D1 can vary between the proximal and distal portions 12a, 12b and the mid-portion 14, e.g., taper to a larger diameter in the mid-portion 14 to allow for presence of the bushing 26.

Figure 5:
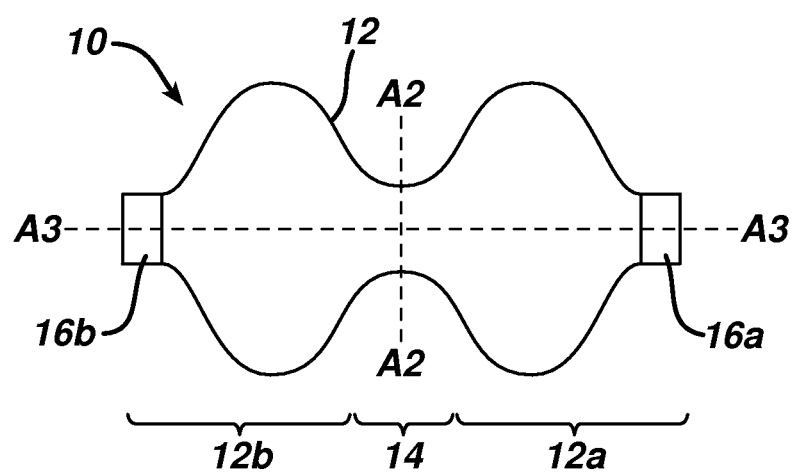
FIG. 5 is a side view of the marking device of FIG. 1 in an expanded position.

FIG. 5 shows the marker 10 in an expanded position. The bushing 26 may or may not be visible in the mid-portion 14, depending on its integration into the tubular body 12. In the expanded position, the marker 10 can have a generally barbell-shape in which the proximal and distal portions 12a, 12b have an increased diameter. The marker 10 can be biased to the expanded position, e.g., to a generally barbell-shape, and it can be elongated into the unexpanded position (e.g., as shown in FIG. 1) for insertion into the body and into marking position proximate to tissue desired for marking. Alternatively, the marker 10 can be manually inflated or deformed to form such a barbell-shape, as discussed further below.

In one embodiment, the expanded proximal and distal portions 12a, 12b can be formed by increasing the volume of the inner pathway 24 in the proximal and distal portions 12a, 12b, such as by increasing a volume and/or pressure of fluid (e.g., air, water, saline, etc.) in the inner pathway 24 in the proximal and distal portions 12a, 12b. In this embodiment, the proximal and distal portions 12a, 12b in the expanded position are substantially ovular or spherical and are configured such that the proximal and distal portions 12a, 12b extend substantially parallel to one another, i.e., they are formed in parallel planes. However, the size and shape of the expanded proximal and distal portions 12a, 12b can vary depending on a variety of factors, such as the size and shape of the tubular body 12 in the proximal and distal portions 12a, 12b, the material composition of the marker 10, the configuration of tissue engaged by the marker 10, etc. The length L2 of the mid-portion 14 can determine the distance between the expanded proximal and distal portions 12a, 12b, at least along the inner surface 28 of the tubular body 12 because the mid-portion 14 is preferably non-expanding. Furthermore, the proximal and distal portions 12a, 12b can generally mirror each other. Expansion of the proximal and distal portions 12a, 12b can occur concurrently or sequentially, e.g., expanding the distal portion 12b before the proximal portion 12a. If the marker 10 is inflated with fluid, the self-sealing ends 16a, 16b can each close (e.g., self-seal or be manually sealed) during or after the marker 10 moves into the expanded position such that the marker 10 can retain its shape in the expanded position. In other words, the sealing of the self-sealing ends 16a, 16b can prevent fluid from escaping out of the inner pathway 24. If the marker 10 deforms to an expanded position, such as by when formed from a shape memory or elastomer material, one or both of the ends 16a, 16b can but need not be self or manually sealed to help hold the marker 10 in the expanded position.

Figure 6:
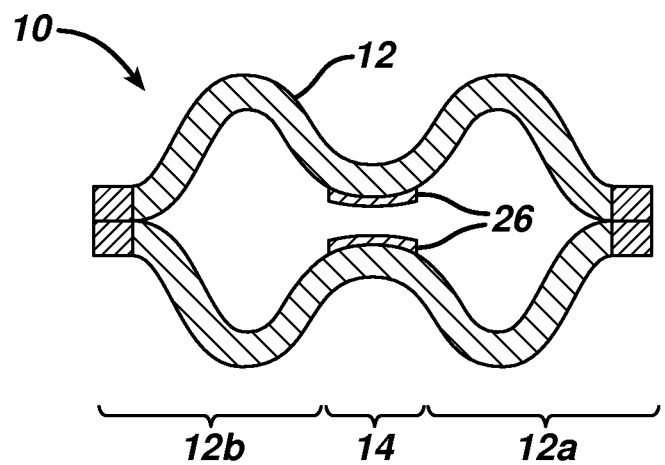
FIG. 6 is a cross-sectional view of the marking device of FIG. 5.

FIG. 6 shows a cross-sectional view of the expanded marker 10 of FIG. 5. In FIG. 6, the bushing 26 in the mid-portion 14 is visible between the expanded proximal and distal portions 12a, 12b.

The marker 10 can be formed from a variety of materials including absorbable and non-absorbable materials. In an exemplary embodiment, the marker 10 is at least partially formed from a deformable material that can undergo deformation (i.e., deformation with negligible elastic component). The marker 10 can be formed from a variety of pliable and non-pliable materials, preferably a biocompatible material safe for use in the body. In an exemplary embodiment, the marker 10 is at least partially made from a shape memory material, such as Nitinol (a nickel-titanium alloy), but the marker 10 can be made from any type of material and any combination of materials able to provide structure to the marker 10 and appropriate for use in the body. Other exemplary shape memory metallic materials include alloys such as copper-zinc-aluminum-nickel, copper-aluminum-nickel, and nickel-titanium. Additional exemplary non-metallic shape memory materials include thermoplastic materials such as Nylon or Nylon blends and shape memory polymers such as Veriflex™. The marker 10 can also be at least partially formed from a bioabsorbable, biocompatible material, such as polydioxanone (PDO or PDS), Vicryl™, and polylactic acid (PLA). However, it is understood that other suitable biocompatible and optionally bioabsorbable polymers can also be used for the marker 10. In a preferred embodiment, the marker 10 can be partially formed from a bioabsorbable, biocompatible material such that the portion of the marker 10 outside a body lumen when disposed in the expanded position (e.g., the marker's distal portion 12b) can be bioabsorbed, thereby allowing a remainder of the marker 10 to "fall" into the body lumen and pass with stool after a desired amount of time. Materials which are not normally radiopaque, e.g., magnesium alloy, can be enhanced and made x-ray visible with the addition of x-ray visible materials, such as particles of iron oxide, stainless steel, titanium, tantalum, platinum, or any other suitable equivalents. The marker 10 can optionally have a drug coating, similar to a drug-eluting stent, that can break down over time to release a drug to, for example, help reduce chances of cell proliferation (e.g., hyperplasia) or reduce other possible adverse effects from the presence of the marker 10 in the body. The marker 10 can have any coloration, such as a dark color (e.g., dark blue, black, etc.) to help enhance its visibility when disposed in a body.

Figure 7:
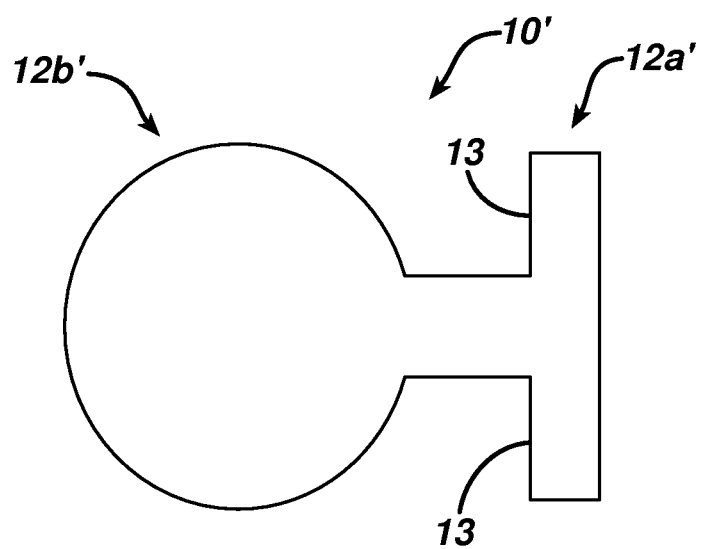
FIG. 7 a side view of another exemplary embodiment of a marking device in a deployed configuration.

Another embodiment of a marker 10' is shown in an expanded position in FIG. 7. The marker 10' is similar to the marker 10 but has a different shape. The marker's distal portion 12b' in the expanded position is substantially ovular or spherical, similar to the distal portion 12b of the marker 10, but the marker's proximal portion 12a' in the expanded position is substantially rectangularly box-shaped. With such a rectangular shape, a distal surface 13 of the proximal portion 12a' in the expanded position can help grasp tissue engaged by the marker 10', similar to the shoulders 20 of the marker 10. While the proximal and distal portions 12a', 12b' can have any size and configuration, the distal portion 12b' of the marker 10' is shown closed or permanently sealed, while the marker's proximal portion 12a' is shown as self-sealing.

A marker can be introduced into a body to mark tissue in a variety of ways. Various devices can be used to deliver the marker proximate to tissue, including rigid and flexible devices, such as elongate shafts, cannulated devices, and guidewires configured to deliver the marker proximate to the tissue. The marker can also be applied manually. While various techniques can be used to deploy the marker in a body and through a tissue wall and to expand the marker, in an exemplary embodiment, the marker in an unexpanded position is disposed in or removably coupled to a delivery device that can be configured to help guide the marker into a body either independently or through an introducer device (e.g., any surgical tool including a cannula or other working channel through which the delivery device can be advanced), to advance the marker through the tissue wall, and to allow expansion of the marker's proximal and distal portions.

Figure 8:
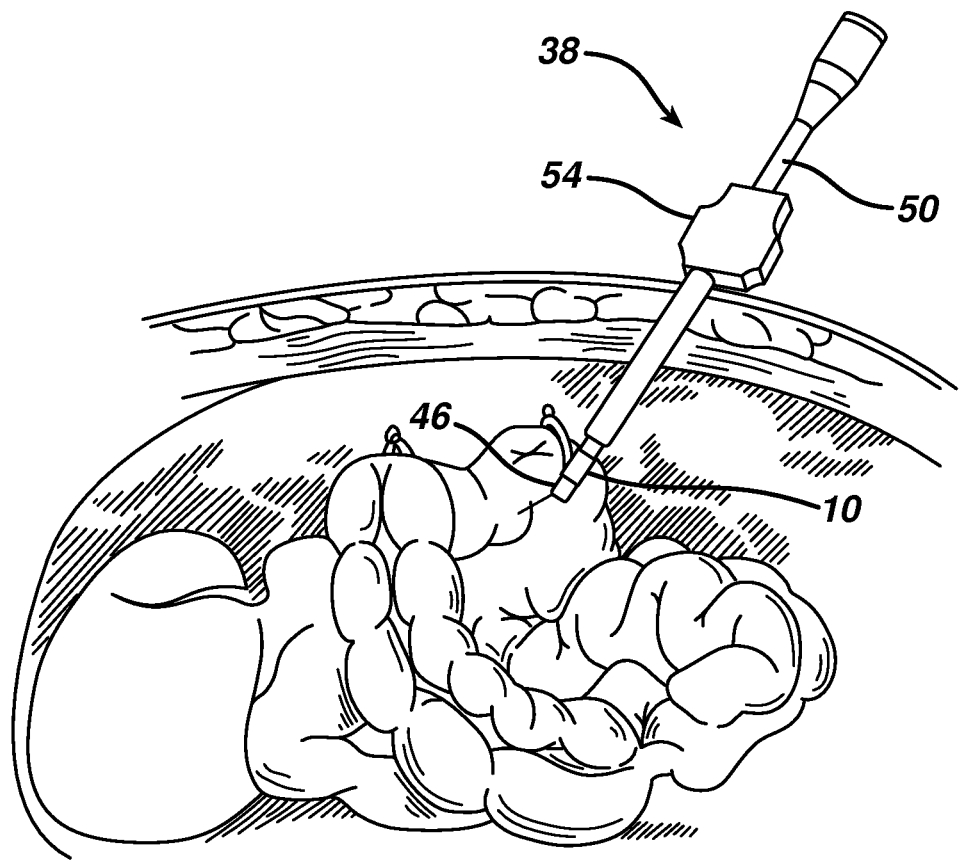
FIG. 8 is a perspective view of one embodiment of an applicator for applying the marking device of FIG. 1 to tissue.

FIG. 8 illustrates one exemplary embodiment of a delivery device 38. As shown, the delivery device 38 has an elongate shaft 50. The elongate shaft 50 can have a variety of configurations, and the particular configuration can vary depending on the mode of insertion. In the illustrated embodiment, the elongate shaft 50 is disposed through a cannula, e.g., a trocar 54, having a working channel that extends into a body cavity. The elongate shaft 50 can also include one or more lumens formed therein and extending between proximal and distal ends thereof. In use, the delivery device 38 can be inserted through the trocar 54 that extends through a tissue surface and into the abdominal cavity (or any other body cavity). As mentioned above, endoscopes or other introducer devices can also optionally be used, and/or the delivery device 38 can be an introducer that is introduced directly through a natural orifice or through a man-made orifice. Once positioned adjacent to a target tissue, the delivery device 38 can be manipulated using, for example, controls to articulate the distal end of the delivery device 38 and controls to advance the marker 10 (or any other marker described herein) off the delivery device's distal end 46. A positioning sleeve can also be used, as discussed below, although it is not illustrated in FIG. 8.

Figure 9:
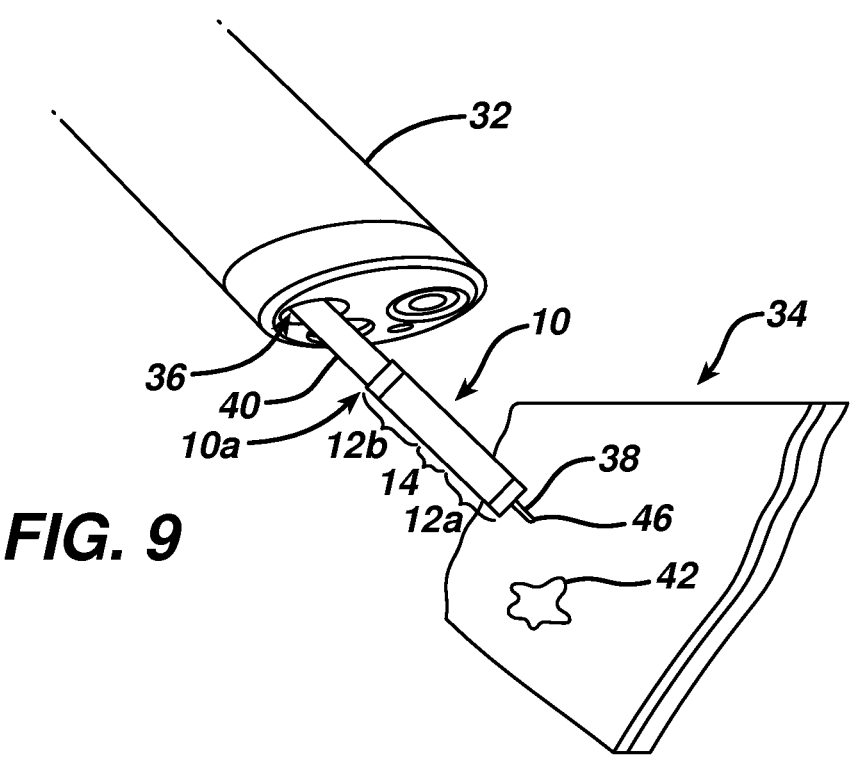
FIG. 9 is a perspective view of another embodiment of an applicator for applying the marking device of FIG. 1 to tissue.

In another exemplary embodiment shown in FIG. 9, an introducer device 32 can be a scope such as an endoscope, laparoscope, and colonoscope, where the introducer device's channel 36 includes a working channel of the scoping device. Alternatively, as mentioned above, the introducer device 32 can include virtually any surgical tool that has a cannulated interior and that is configured to be inserted into a body. In the event that the surgical tool used with the invention is a colonoscope, it can be any flexible, elongate member that is capable of being inserted into the body, such as through a natural orifice, through a puncture hole formed in tissue, and in any other way appreciated by a person skilled in the art.

In general, the introducer 32 includes at least one working channel 36 extending therethrough that the marker 10 can be advanced through toward a tissue wall 34. In one embodiment, the marker 10 can be advanced into the body through the working channel 36 along a guidewire. The guidewire can also extend through the tissue wall 34 and be used to guide the marker 10 in an unexpanded position through the tissue wall 34. In another embodiment, the marker 10 in an unexpanded position can be advanced directly through the introducer's working channel 36, or the marker 10 can be disposed within a tool having a cannulated interior, and the cannulated tool can be disposed and advanced through the introducer's working channel 36. Because the marker 10 can be pliable (at least in its unexpanded position), the marker 10 can be compressed, folded, or otherwise manipulated to advance through the working channel 36 and/or the cannulated tool in any way, as will be appreciated by those skilled in the art.

The external diameter of the delivery device can be chosen for a given marker's shape and size to be small enough to allow passage of the marker 10 over its exterior (or alternatively within its lumen) but large enough to prevent the marker 10 from substantially moving into the expanded position (particularly if the marker 10 is biased to the expanded position) before the marker 10 has been at least partially advanced off the distal end of the delivery device.

The delivery device can optionally be detachably coupled to the marker 10 to help prevent the marker 10 from prematurely advancing off the delivery device's distal end. Examples of detachable coupling mechanisms include a clasp, a clamp, a hook, interlocking protrusions/depressions, threads, friction, an indentation in the positioning sleeve that at least a portion of the marker's proximal portion 12*a* can fit into, etc.

As mentioned above, in an exemplary embodiment, the marker 10 can be advanced through the introducer's working channel 36 by being slidably disposed in the unexpanded position around the delivery device 38. Also as mentioned above, the marker 10 can optionally be detachedly coupled to the delivery device 38 with a detachable coupling mechanism. The delivery device 38 can be disposed in and advanced through the introducer's working channel 36 with the marker 10 disposed around a distal portion of the delivery device 38. A positioning sleeve 40 (FIGS. 10-14), e.g., a push rod or driver, slidably disposed around the delivery device 38 and disposed proximate to the proximal portion 12*a* of the marker 10 can be used to advance and/or push the marker 10 from the delivery device 38, as discussed further below. If the distal end 10*b* of the marker 10 is closed or permanently sealed as mentioned above and shown, for example, in the marker 10' of FIG. 7, then the positioning sleeve 40 can optionally be omitted and the delivery device 38 can be used to advance the marker 10 into position through the tissue wall 34. In other words, a distal end 46 of the delivery device 38 can abut the distal end 10*b* of the marker 10 from within the inner pathway 24 against the tubular body's inner surface 28 such that distally advancing the delivery device 38 pushes against the closed distal end 10*b* of the marker 10 to also distally advance the marker 10. In such a case, the delivery device's distal end 46 is preferably blunt or otherwise non-cutting to help prevent it from puncturing the marker's distal end 10*b* as the distal end 46 is pushed against the marker's distal end 10*b*.

The positioning sleeve 40 can have a variety of configurations, but it is preferably adapted to engage at least a portion of the proximal portion 12*a* of the marker 10. While various techniques can be used to engage marker 10 with the positioning sleeve 40, FIGS. 10-14 illustrate one exemplary technique. As shown, the positioning sleeve 40 abuts the proximal portion 12*a* of the marker 10 at the proximal end 10*a* such that advancing the positioning sleeve 40 toward the delivery device's distal end 46 can also advance the marker 10. In other embodiments, the positioning sleeve 40 can engage the marker 10 through a detachable coupling mechanism. With the marker 10 and the positioning sleeve 40 engaged with a detachable coupling mechanism, the positioning sleeve 40 can also be used to proximally move the marker 10, thereby allowing for more flexibility in positioning the marker 10 because the positioning sleeve 40 can be used to move the marker 10 in multiple directions.

The delivery device 38 and the positioning sleeve 40 can be rigid or flexible and made from any combination of (preferably biocompatible) materials. The positioning sleeve 40 can be configured to provide maximum flexibility during clinical use, while the delivery sleeve 38 can be rigidly configured to provide structural support to the positioning sleeve 40 and/or the marker 10 when the positioning sleeve 40 and/or the marker 10 are disposed thereon. For example, the positioning sleeve 40 can be formed from a flexible material, or the positioning sleeve 40 can include one or more flexible regions formed thereon. Such configurations provide flexibility along all or portions of the positioning sleeve 40 (and/or the tubular body 12 of the marker 10, which is also at least partially pliable as discussed above), but can also ensure that force applied to one end of the positioning sleeve 40 will be transmitted along its length to the other end. Furthermore, the delivery device 38 and/or the positioning sleeve 40 can be made from a material more flexible than a material used for the introducer 32 (if used), thereby allowing the delivery device 38 and/or the positioning sleeve 40 to be more easily positioned within a body lumen 44 than the introducer 32.

The marker 10, the positioning sleeve 40, and/or the delivery device 38 can be disposed within the introducer 32 at any point before or after the introducer 32 has been introduced into the body lumen 44, including before or after the introducer 32 has been positioned at a desired position proximate to a tissue to be removed from the tissue wall 34 or otherwise examined. Preferably, the delivery device 38 is advanced through the introducer's working channel 36 after the tissue to be marked has been identified because in some surgical procedures, no tissue to be marked is identified and hence no need exists to use the marker 10. Although, in some embodiments, the delivery device 38, the positioning sleeve 40, and/or the marker 10 can be pre-loaded into the introducer 32. Similarly, the marker 10 and the positioning sleeve 40 can each be disposed around the delivery device 38 at any point before or after the delivery device 38 has been advanced through the introducer's working channel 36.

Figure 10:
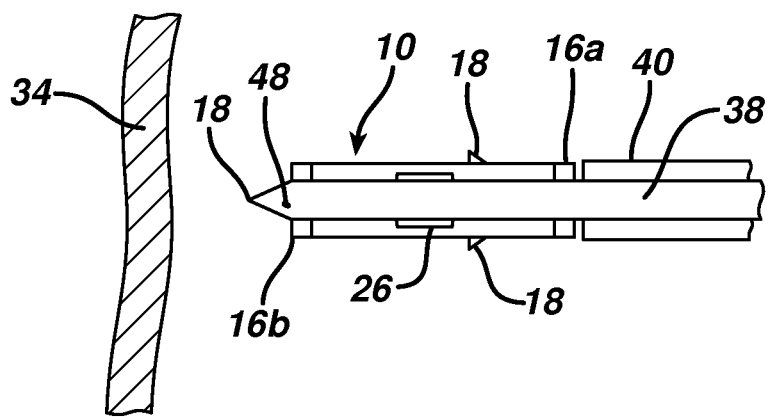
FIG. 10 is a side view of one embodiment of an introducer device having a delivery device disposed therein for, showing the delivery device about to be inserted through tissue with the marking device of FIG. 1 disposed therearound.
Figure 11:
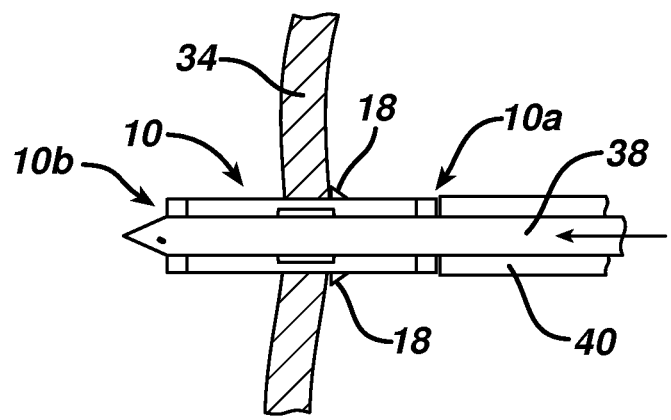
FIG. 11 is a cross-sectional view of the marking device and the delivery device of FIG. 10 advanced through the tissue wall.

FIGS. 10-14 illustrate a distal portion of the delivery device 38 and the positioning sleeve 40 in use with the marker 10. Following expansion of the marker 10, the delivery device 38 and the positioning sleeve 40 are preferably removed from the patient. In general, the introducer 32 and the delivery device 38 are positioned to allow the marker's placement proximate to the tissue to be marked, as shown in FIG. 10, and the marker 10 can be introduced through the tissue wall 34, as shown in FIG. 11. The distal end 46 of the delivery device 38 can include a pointed tip which can be used to puncture the tissue wall 34 to help ease passage of the delivery device 38 and the marker 10 through the tissue wall 34. Alternatively or in addition, another cutting element can be used to puncture the tissue wall 34, e.g., a knife, a needle, or a pin disposed through another working channel of the introducer 32 or through the working channel 36 of the delivery device.

Figure 12:
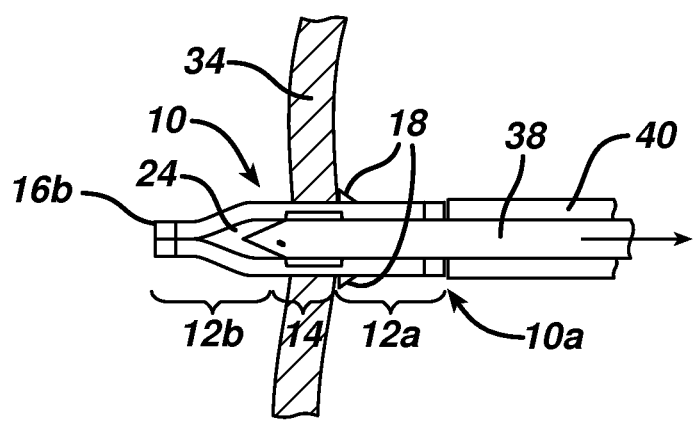
FIG. 12 is a cross-sectional view of the marking device and delivery device of FIG. 11 showing the delivery device being withdrawn to deploy the marking device.

Generally, the marker 10 can be advanced down the delivery device 38 toward the delivery device's distal end 46 while disposed around the delivery device 38, as shown in FIG. 12. The marker 10 can be pushed or otherwise advanced down the delivery device 38, such as by manipulating the positioning sleeve 40. At any time after the marker 10 has been advanced into the body lumen 44 and in a desirable location with respect to the tissue wall 34, the marker 10 can be disengaged from the positioning sleeve 40 if the marker 10 and the positioning sleeve 40 are detachably coupled, or, as in this illustrated embodiment, the marker's proximal portion 12a can merely abut the positioning sleeve 40.

The marker 10 is preferably positioned with respect to the tissue wall 34 such that the marker's mid-portion 14 (e.g., a non-pliable, non-expanding portion of the tubular body 12) substantially aligns with the tissue wall 34. The marker 10 can also optionally be positioned such that placement of its proximal and distal portions 12a, 12b can ensure correct line of resection when removing the tissue to be removed. As discussed above, if one or more shoulders 18 are present, the shoulders 18 can prevent movement of the marker 10 in a distal direction once the marker 10 has advanced a sufficient distance through the tissue wall 34 such that one or more of the shoulders 18 engage or abut the tissue wall 34, thereby helping to stop distal movement of the marker 10 beyond a certain point along the tubular body's length L and substantially align the mid-portion 14 with the tissue wall 34, as shown in FIG. 12. Furthermore, whether the marker 10 is biased to the expanded position or not, the position of the marker 10 with respect to the tissue wall 34 can be manually adjusted using any appropriate tool (e.g., surgical instruments, one's fingertips, etc.), preferably before the marker 10 has moved to the expanded position.

The marker 10 can be positioned any distance away from a tissue to be removed or otherwise examined, although the distance is preferably of a value small enough such that any incision into or any examination of the body lumen 44 at the location of the marker 10 allows for relatively easy identification of the tissue. In some embodiments, the marker 10 (in the unexpanded and/or expanded positions) can directly engage at least a portion of the desired tissue. Once the marker 10 has been positioned in the expanded position through the tissue wall 34, the distance between the marker 10 and the tissue remains substantially unchanged until the marker 10 is absorbed by the body, the marker 10 is removed from the body, the tissue grows or otherwise mutates, or the tissue is removed from the body. In other words, the marker's position is substantially static once the marker 10 is in the expanded position through the tissue wall 34. In this way, the marker 10 can remain adjacent to the tissue and accurately mark the location of the tissue until the marker 10 is absorbed by the body, the marker 10 is removed from the body, or the tissue 14 is removed from the body. Furthermore, two markers 10 can be positioned a distance apart in the same or separate tissues to indicate a length of tissue to be removed or otherwise examined, while three or more markers 10 can be positioned through the same or separate tissues to indicate an area or volume of tissue to be removed or otherwise examined.

Figure 13:
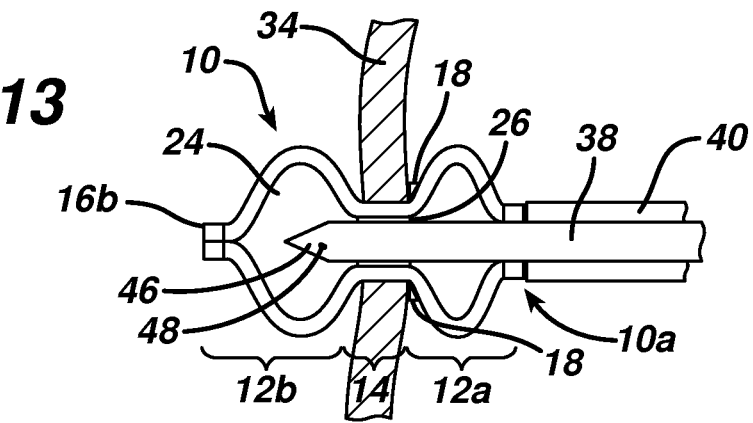
FIG. 13 is a cross-sectional view of the marking device of FIG. 12 in an expanded position with the delivery device of FIG. 12 partially removed therefrom.

With the marker 10 positioned at a desired expansion location, the delivery device 38 can begin to be withdrawn from the marker 10 in a proximal direction (indicated by the directional arrow in FIG. 12), with the positioning sleeve 40 holding the marker 10 in place with respect to the tissue wall 34. Following the delivery device's movement through the marker's distal end 10b, the distal self-sealing end 16b can self-seal, as shown in FIGS. 12 and 13, with the delivery device 38 no longer providing a barrier in the pathway 24 at the distal end 10b (which is no longer open). If the distal end 10b is not self-sealing, the distal end 10b can be otherwise sealed, e.g., stapled, bonded with adhesive, sewn shut with sutures, etc., following removal of the delivery device 38 from the distal end 10b.

The delivery device 38 can be partially withdrawn from the marker 10 such that an inflation port 48 proximal to the distal tip 46 of the delivery device 38 is disposed within the inner pathway 24 of the marker 10. The delivery device's inflation port 48 is shown in FIG. 12 substantially positioned at a junction of the marker's distal portion 12a and mid-portion 14, but the delivery device's inflation port 48 can be positioned anywhere within the marker's inner pathway 24.

Once the inflation port 48 has been positioned within the pathway 24, which effectively includes two sealed ends (because of the sealed distal end 16b and the delivery device 38 disposed within the proximal end 10a), the delivery device 38 can inflate the marker 10 to the expanded position by introducing a fluid into the inner pathway 24 via the inflation port 48, as illustrated in FIG. 13. Any amount of fluid can be introduced into the inner pathway 24 to expand the marker 10 to any desired pressure and/or any desired size. Any type of fluid can be used to inflate the marker 10, and the fluid can optionally include a drug (similar to the drug coating mentioned above) that can be released outside the marker 10 when the marker 10 breaks down for bioabsorption and/or through one or more porous members in the marker's distal portion 12b, proximal portion 12a, and/or mid-portion 14. The type of material used for the marker 10 can help determine the time and/or location release of such a drug, e.g., by using a bioabsorbable material in one or both of the marker's proximal and distal portions 12a, 12b to help control release of the drug on one or both sides of the tissue wall 34. The bushing 26 can allow inflation of both the proximal and distal portions 12a, 12b despite even a partial presence of the delivery device 38 in the inner pathway 24 in the mid-portion 14. In other words, fluid introduced through the inflation port 48 into the inner pathway 24 in the distal portion 12b can pass through the bushing 26 in the mid-portion 14 to enter the inner pathway 24 in the proximal portion 12a. The reverse can also hold true, with fluid introduced through the inflation port 48 into the inner pathway 24 in the proximal portion 12a passing through the bushing 26 in the mid-portion 14 to enter the inner pathway 24 in the distal portion 12b. Alternatively, the proximal and distal portions 12a, 12b can be independently expanded, such as by the inflation port 48 being positioned within the inner pathway 24 in each one of the proximal and distal portions 12a, 12b and expanding each portion independently (although not necessarily sequentially since the inflation port 48 can inflate one portion by any amount, be positioned to inflate the other portion by any amount, be repositioned in the first portion for further inflation, etc.). In addition to being configured to introduce fluid into the inner pathway 24, the inflation port 48 can also be configured to allow fluid removal from the inner pathway 24. In this way, the expansion shape, pressure, and size of the proximal and distal portions 12a, 12b can be better adjusted.

With the marker 10 in or moving into the expanded position, the marker's shoulders 18 (if present) can be pushed against the tissue wall 34 by the expanded or expanding proximal portion 12a, depending on the configuration of the shoulders 18, the tissue wall 34, and/or the proximal portion 12a. As such, the shoulders 18 can be configured to act in any number of ways when the marker 10 is in or is moving into the expanded position. For example, the shoulders 18, if made from a pliable material, can at least partially bend, collapse, fold, or otherwise flatten into itself and/or the marker's tubular body 12 so as to not expound undue pressure on the tissue wall 34, the marker's proximal portion 12a, and/or the marker's mid-portion 14. The shoulders 18 could alternatively grasp the tissue wall 34 (e.g., with the tissue engaging mechanisms 20) to help secure the marker 10 in place in the expanded position. The shoulders 18 in the embodiment shown in FIG. 13 have been compressed between the tissue wall 34 and the marker 10 by the proximal portion's expansion.

Figure 14:
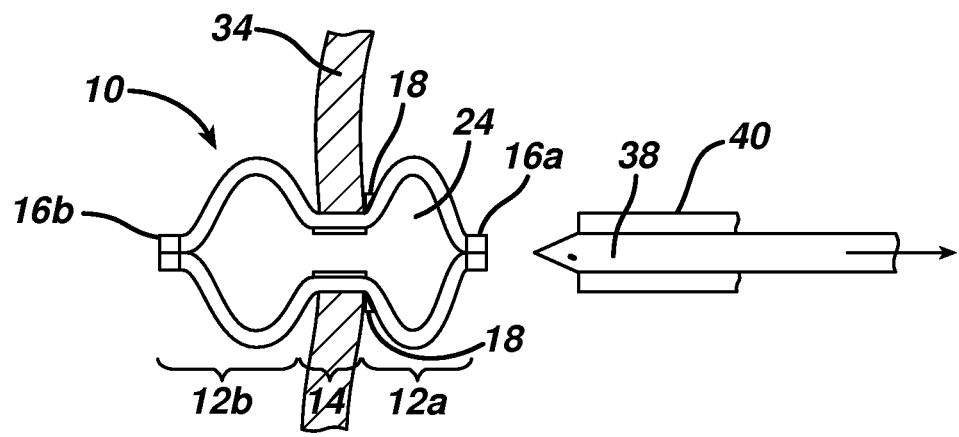
FIG. 14 is a cross-sectional view of the marking device of FIG. 13 fully deployed with the delivery device of FIG. 12 withdrawn therefrom.

Once the marker 10 has reached a desired expanded position, the delivery device 38 can be withdrawn from the marker 10 in a proximal direction as shown by the directional arrow in FIG. 14. The positioning sleeve 40 can also be withdrawn in a proximal direction, either separately from the delivery device 38 or in tandem. Following the delivery device's withdrawal through the marker's proximal end 10a, the proximal self-sealing end 16a can self-seal (or, if not self-sealing, be otherwise sealed), with the delivery device 38 no longer providing a barrier in the pathway 24 at the proximal end 10a (which is no longer open), thereby leaving the marker 10 deployed and engaging the tissue wall 34 in the expanded position.

The proximal and distal portions 12a, 12b are shown in FIG. 14 substantially mirroring each other, e.g., having substantially the same inflated sizes and substantially ovular shapes, but the proximal and distal portions 12a, 12b can vary in expanded size and/or shape. For example, tissue not part of the body lumen 44 and positioned near the tissue wall 34 can abut one of the proximal and distal portions 12a, 12b in the expanded position and prevent that one of the proximal and distal portions 12a, 12b from expanding to the same size and/or shape as the other one of the proximal and distal portions 12a, 12b.

Alternatively, if the marker 10 is biased to the expanded position, the proximal and distal portions 12a, 12b can, but need not be, inflated via the inflation port 48. Instead, withdrawing the delivery device 38 from the tubular body's inner pathway 24 can cause the proximal and distal portions 12a, 12b of the marker 10 to expand, with the distal portion 12b preferably expanding prior to the proximal portion 12a since the delivery device 38 preferably exits the inner pathway 24 starting in the distal portion 12b. In other words, once the structural force provided to the marker 10 by the delivery device 38 is removed, the marker 10 can move from the unexpanded position to the expanded position and the self-sealing ends 16a, 16b, if present, can self-seal (or be manually sealed). If a shape memory material has been used to form the marker 10, any of the proximal and distal portions 12a, 12b and/or the proximal and distal self-sealing ends 16a, 16b can be heat set (at any time or times) to deform the marker 10 into the expanded position.

Figure 15:
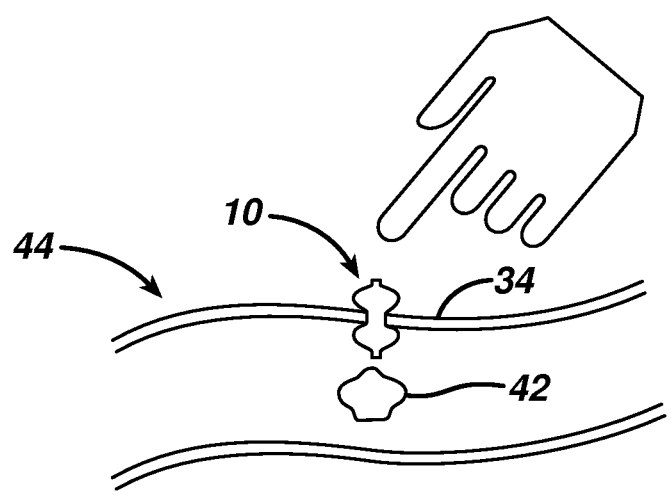
FIG. 15 is a perspective view of the marking device of FIG. 14 being palpably identified in a body lumen.

Once the marker 10 has been disposed in the expanded position through the tissue wall 34, the marker 10 can be left in such a expanded position proximate to the desired tissue after devices such as the introducer 32 and the delivery device 38 have been removed from the body lumen 44. The marker 10 can then be palpably located, as illustrated in an embodiment in FIG. 15, to help locate the desired tissue. The marker 10 can be palpably located directly as shown, or the marker 10 can be palpably located through one or more layers of tissue adjacent to the body lumen 44, e.g., from outside a patient's body. As mentioned above, the marker 10 can also or instead be visually located. Visual observation of the marker 10 can include any one or more of observing the expanded distal portion 12a outside the body lumen 44, observing the expanded proximal portion 12b inside the body lumen 44, viewing still or moving images obtained by a scoping device disposed within the body lumen 44, viewing an x-ray, viewing a barium image, viewing interaction with magnetic particles (if the marker 10 includes a magnetized component), tracing radiopharmaceuticals, etc.

The marker 10 can remain disposed through the tissue wall 34 of the body lumen 44 for any length of time, e.g., twenty-four hours, two days, one week, three weeks, one month, etc. Being safe for use in the body, the marker 10 could remain disposed through the tissue wall 34 indefinitely, but preferably, the marker 10 is either bioabsorbed, naturally removed, or manually removed from the body after it has been used to locate the desired tissue. The length of time the marker 10 remains disposed through the tissue wall 34 can depend on any number of factors, such as the marker's material composition. Even if the marker 10 is fully or partially bioabsorbable, the marker 10 can be removed from the body lumen 44 after it has been used to locate the desired tissue and/or after the tissue has been removed from the body lumen 44, during which procedure the marker 10 can also be removed from the body lumen 44. Any sutures being used to help secure the marker 10 to the body lumen 44 can be disengaged from the body lumen 44 and/or the marker 10, and the marker 10 can be removed from the body. For example, the tubular body 12 of the marker 10 can be cut, punctured, or otherwise broken such that fluid contained in the inner pathway 24 can escape, thereby allowing the marker 10 to move from the expanded position to the unexpanded or other collapsed position such that it can be more easily removed from the tissue wall 34. For another example, the delivery device 34 can be reintroduced into the inner pathway 24 of the marker 10 through one of the proximal and distal self-sealing ends 16a, 16b, and fluid can be withdrawn from the inner pathway 24 through the inflation port 48, thereby allowing the marker 10 to move from the expanded position to the unexpanded or other collapsed position.

If the marker 10 is not being used to mark tissue in a tubular structure but to otherwise mark tissue on a tissue surface, the marker 10 can function and be introduced to tissue in a way similar to any way described above. For example, the marker 10 can be disposed around the delivery device 38, which is disposed in one of the introducer's working channels 36, and be advanced on the delivery device 38 through a tissue surface proximate to a tissue to be removed from the tissue surface. The marker 10 can then move to the expanded position while disposed through the tissue surface, as discussed above.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for marking tissue, comprising:
   identifying tissue to be removed;
   positioning a marker through a tissue wall proximate to the tissue to be removed; and
   expanding proximal and distal portions of the marker on opposing sides of the tissue wall such that the proximal and distal portions engage tissue therebetween, wherein the marker identifies the tissue to be removed;
   wherein positioning the marker comprises advancing a delivery device inserted through an inner pathway of the marker through the tissue wall to position the proximal and distal portions of the marker on opposing sides of the tissue wall.

2. The method of claim 1, wherein expanding each of the proximal and distal portions comprises inflating the proximal and distal portions.

3. The method of claim 1, wherein expanding each of the proximal and distal portions comprises permanently deforming the proximal and distal portions.

4. The method of claim 1, further comprising, after expanding the proximal and distal portions, palpably identifying the marker to locate the tissue to be removed.

5. The method of claim 1, further comprising, after expanding the proximal and distal portions, visually identifying the marker to locate the tissue to be removed.

6. The method of claim 1, wherein the tissue wall comprises a bowel wall.

\* \* \* \* \*